(12) United States Patent
Rolando et al.

(10) Patent No.: US 9,895,225 B2
(45) Date of Patent: Feb. 20, 2018

(54) COLLAPSIBLE VALVE PROSTHESIS (71) Applicant: Sorin Group Italia S.r.l., Milan (IT)

(72) Inventors: Giovanni Rolando, Chivasso (IT);
Paolo Gaschino, Castagneto Po (IT);
Antonella Orecchia, Turin (IT);
Monica Achiluzzi, Chivasso (IT);
Massimiliano Ares, Collegno (IT)

(73) Assignee: Sorin Group Italia S.r.l., Milan (IT)

( * ) Notice: Subject to any disclaimer, the term of this patent is extended or adjusted under 35 U.S.C. 154(b) by 0 days.

(21) Appl. No.: 13/835,508

(22) Filed: Mar. 15, 2013

(65) Prior Publication Data
US 2013/0253643 A1 Sep. 26, 2013

(30) Foreign Application Priority Data

Mar. 23, 2012 (EP) ..................................... 12425060

(51) Int. Cl.
*A61F 2/24* (2006.01)

(52) U.S. Cl.
CPC .......... *A61F 2/2445* (2013.01); *A61F 2/2409* (2013.01); *A61F 2/2418* (2013.01);
(Continued)

(58) Field of Classification Search
CPC ........ A61F 2/24; A61F 2/2412; A61F 2/2415; A61F 2/2418; A61F 2/2451; A61F 2/243;
(Continued)

(56) References Cited

U.S. PATENT DOCUMENTS 5,855,601 A 1/1999 Bessler et al.
6,287,339 B1 9/2001 Vazquez et al.
(Continued)

FOREIGN PATENT DOCUMENTS

CN 102869319 A 1/2013
EP 0133420 B1 2/1988
(Continued)

OTHER PUBLICATIONS

European Search Report issued in EP Application No. 12425060, completed Jun. 27, 2012, 7 pages.
(Continued)

*Primary Examiner* — David Isabella
*Assistant Examiner* — Rokhaya Diop
(74) *Attorney, Agent, or Firm* — Faegre Baker Daniels LLP (57) ABSTRACT

A collapsible valve prosthesis includes an armature and a set of prosthetic valve leaflets supported by the armature. The armature is expandable from a contracted condition to an expanded condition for anchoring at an annulus of a natural valve site, and includes a tubular intra-annular portion defining a blood flow lumen having an inflow side and an outflow side. The tubular intra-annular portion supports the prosthetic valve leaflets in the blood flow lumen and is provided with outward formations for coupling with the natural valve site. The armature includes an over-annular portion linked to the intra-annular portion to extend collar-like over the annulus of the natural valve site at the inflow side of the blood flow lumen. The armature may also include an under-annular portion to extend collar-like at the outflow side of the blood flow lumen. The prosthesis may permit mitral valve replacement (MVR) without removing the native valve leaflets and the chordae tendineae.

20 Claims, 4 Drawing Sheets

(52) U.S. Cl.
CPC .......... *A61F 2/2433* (2013.01); *A61F 2/2436* (2013.01); *A61F 2220/0016* (2013.01); *A61F 2230/005* (2013.01); *A61F 2230/008* (2013.01); *A61F 2230/0054* (2013.01); *A61F 2230/0067* (2013.01); *A61F 2230/0078* (2013.01); *A61F 2250/0048* (2013.01)

(58) Field of Classification Search
CPC .... A61F 2/2433; A61F 2/2445; A61F 2/2409; A61F 2/2436; A61F 2230/0078; A61F 2230/0067; A61F 2230/0054; A61F 2230/008; A61F 2230/005; A61F 2220/016; A61F 2250/0048
USPC ......... 623/2.37, 2.12, 2.14, 2.17, 2.18, 2.38, 623/1.24, 2.1, 2.13, 2.15, 2.16
See application file for complete search history.

(56) References Cited

U.S. PATENT DOCUMENTS

| | | |
|---|---|---|
| 6,312,465 B1 | 11/2001 | Griffin et al. |
| 6,425,916 B1 | 7/2002 | Garrison et al. |
| 6,458,153 B1 | 10/2002 | Bailey et al. |
| 6,461,366 B1 | 10/2002 | Seguin |
| 6,530,952 B2 | 3/2003 | Vesely |
| 6,569,196 B1 | 5/2003 | Vesely |
| 6,629,534 B1 | 10/2003 | St. Goar et al. |
| 6,821,297 B2 | 11/2004 | Snyders |
| 6,974,476 B2 | 12/2005 | McGuckin, Jr. et al. |
| 7,011,681 B2 | 3/2006 | Vesely |
| 7,018,406 B2 | 3/2006 | Seguin et al. |
| 7,018,408 B2 | 3/2006 | Bailey et al. |
| 7,252,682 B2 | 8/2007 | Seguin |
| 7,329,278 B2 | 2/2008 | Seguin et al. |
| 7,381,220 B2 | 6/2008 | Macoviak et al. |
| 7,556,646 B2 | 7/2009 | Yang et al. |
| 7,585,321 B2 | 9/2009 | Cribier |
| 7,648,528 B2 | 1/2010 | Styrc |
| 7,708,775 B2 | 5/2010 | Rowe et al. |
| 7,717,955 B2 | 5/2010 | Lane et al. |
| 7,753,949 B2 | 7/2010 | Lamphere et al. |
| 7,758,640 B2 | 7/2010 | Vesely |
| 7,776,083 B2 | 8/2010 | Vesely |
| 7,806,927 B2 | 10/2010 | Styrc |
| 7,892,281 B2 | 2/2011 | Seguin et al. |
| 7,959,672 B2 | 6/2011 | Salahieh et al. |
| 8,016,882 B2 | 9/2011 | Macoviak et al. |
| 8,025,695 B2 | 9/2011 | Fogarty et al. |
| 8,048,153 B2 | 11/2011 | Salahieh et al. |
| 8,070,802 B2 | 12/2011 | Lamphere et al. |
| 8,105,375 B2 * | 1/2012 | Navia et al. ............... 623/2.1 |
| 8,167,935 B2 | 5/2012 | McGuckin, Jr. et al. |
| 8,221,493 B2 | 7/2012 | Boyle et al. |
| 8,236,049 B2 | 8/2012 | Rowe et al. |
| 8,287,591 B2 | 10/2012 | Keidar et al. |
| 8,323,335 B2 | 12/2012 | Rowe et al. |
| 8,398,708 B2 | 3/2013 | Meiri et al. |
| 8,403,983 B2 * | 3/2013 | Quadri et al. ............... 623/2.17 |
| 8,414,644 B2 | 4/2013 | Quadri et al. |
| 8,449,599 B2 * | 5/2013 | Chau et al. ............... 623/1.26 |
| 8,454,686 B2 | 6/2013 | Alkhatib |
| 8,540,767 B2 | 9/2013 | Zhang |
| 8,579,964 B2 | 11/2013 | Lane et al. |
| 8,579,966 B2 * | 11/2013 | Seguin et al. ............. 623/2.18 |
| 8,597,348 B2 | 12/2013 | Rowe et al. |
| 9,186,249 B2 | 11/2015 | Rolando et al. |
| 2005/0137691 A1 | 6/2005 | Salahieh et al. |
| 2005/0182486 A1 | 8/2005 | Gabbay |
| 2006/0195183 A1 | 8/2006 | Navia et al. |
| 2007/0043435 A1 | 2/2007 | Seguin et al. |
| 2008/0140189 A1 | 6/2008 | Nguyen et al. |
| 2008/0208327 A1 * | 8/2008 | Rowe ........................ 623/2.11 |
| 2009/0125098 A1 | 3/2009 | Chuter |
| 2009/0248149 A1 * | 10/2009 | Gabbay ....................... 623/2.37 |
| 2009/0276040 A1 | 11/2009 | Rowe et al. |
| 2010/0004739 A1 | 1/2010 | Vesely |
| 2010/0145440 A1 | 6/2010 | Keranen |
| 2010/0174363 A1 | 7/2010 | Castro |
| 2010/0256741 A1 * | 10/2010 | Hansen ........................ 623/1.16 |
| 2010/0312333 A1 | 12/2010 | Navia et al. |
| 2011/0029072 A1 * | 2/2011 | Gabbay ....................... 623/2.23 |
| 2011/0071624 A1 | 3/2011 | Finch et al. |
| 2011/0098800 A1 | 4/2011 | Braido et al. |
| 2011/0137397 A1 * | 6/2011 | Chau ..................... A61F 2/2418 623/1.11 |
| 2011/0166636 A1 * | 7/2011 | Rowe ........................... 623/1.11 |
| 2011/0178597 A9 | 7/2011 | Navia et al. |
| 2011/0218620 A1 | 9/2011 | Meiri et al. |
| 2011/0224785 A1 * | 9/2011 | Hacohen ..................... 623/2.18 |
| 2011/0313515 A1 | 12/2011 | Quadri et al. |
| 2012/0010697 A1 * | 1/2012 | Shin et al. ................... 623/1.26 |
| 2012/0016464 A1 | 1/2012 | Seguin |
| 2012/0022640 A1 * | 1/2012 | Gross et al. ................. 623/2.11 |
| 2012/0046742 A1 | 2/2012 | Tuval et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0303116 A1 | 11/2012 | Gorman et al. |
| 2013/0018449 A1 | 1/2013 | Bailey et al. |
| 2013/0035759 A1 | 2/2013 | Gross et al. |
| 2013/0053950 A1 | 2/2013 | Rowe et al. |
| 2013/0144381 A1 | 6/2013 | Quadri et al. |
| 2013/0211508 A1 | 8/2013 | Lane et al. |
| 2013/0245753 A1 | 9/2013 | Alkhatib |
| 2014/0046434 A1 | 2/2014 | Rolando et al. |

FOREIGN PATENT DOCUMENTS

| | | |
|---|---|---|
| EP | 0155245 B1 | 5/1990 |
| EP | 0515324 B1 | 12/1996 |
| EP | 1233731 B1 | 11/1999 |
| EP | 1049425 B1 | 11/2000 |
| EP | 1176913 B1 | 2/2002 |
| EP | 1251803 B1 | 10/2002 |
| EP | 1335683 B1 | 8/2003 |
| EP | 1343438 B1 | 9/2003 |
| EP | 1401359 B1 | 3/2004 |
| EP | 1408850 B1 | 4/2004 |
| EP | 1562522 B1 | 8/2005 |
| EP | 1621162 B1 | 2/2006 |
| EP | 1701668 B1 | 9/2006 |
| EP | 1758523 B1 | 3/2007 |
| EP | 1935378 A1 | 6/2008 |
| EP | 1690515 B1 | 7/2008 |
| EP | 2000115 B1 | 12/2008 |
| EP | 2072027 A1 | 6/2009 |
| EP | 2078498 B1 | 7/2009 |
| EP | 2138132 B1 | 12/2009 |
| EP | 2250976 A1 | 11/2010 |
| EP | 2258312 B1 | 12/2010 |
| EP | 2260796 B1 | 12/2010 |
| EP | 2260797 B1 | 12/2010 |
| EP | 2260798 B1 | 12/2010 |
| EP | 2340075 B1 | 7/2011 |
| EP | 2641569 A1 | 3/2012 |
| EP | 2476394 B1 | 7/2012 |
| EP | 2486893 A1 | 8/2012 |
| EP | 2526895 B1 | 11/2012 |
| EP | 2526898 B1 | 11/2012 |
| EP | 2526899 B1 | 11/2012 |
| EP | 2529696 B1 | 12/2012 |
| EP | 2529697 B1 | 12/2012 |
| EP | 2529698 B1 | 12/2012 |
| EP | 2529699 B1 | 12/2012 |
| EP | 2537487 B1 | 12/2012 |
| EP | 2886083 A1 | 6/2015 |
| WO | WO2008091515 A2 | 7/2008 |
| WO | WO2011044994 A1 | 4/2011 |
| WO | WO2012063228 A1 | 5/2012 |
| WO | WO2013037805 A1 | 3/2013 |
| WO | WO2013075215 A1 | 5/2013 |

(56) References Cited

FOREIGN PATENT DOCUMENTS

| WO | WO2013082454 A1 | 6/2013 |
|---|---|---|
| WO | WO2013096541 A1 | 6/2013 |
| WO | 2013128436 A1 | 9/2013 |

OTHER PUBLICATIONS

European Search Report issued in EP Application No. 12425139, completed Jan. 16, 2013, 7 pages.
European Search Report issued in EP Application No. 13425113, dated Feb. 7, 2014, 6 pages.
International Search Report issued in PCT/IB2013/052090, dated Jul. 21, 2013, 4 pages.
International Search Report issued in PCT/IB2014/063176, dated Oct. 9, 2014, 12 pages.
International Preliminary Report on Patentability issued in PCT/IB2014/061436, dated Nov. 24, 2016, 7 pages.
International Preliminary Report on Patentability issued in PCT/IB2014/063176, dated Feb. 18, 2016, 9 pages.
International Search Report and Written Opinion issued in PCT/IB2014061436, dated Oct. 20, 2014, 9 pages.

\* cited by examiner

COLLAPSIBLE VALVE PROSTHESIS

CROSS-REFERENCE TO RELATED APPLICATION

This application claims priority to European Application No. 12425060.6, filed Mar. 23, 2012, which is herein incorporated by reference in its entirety.

TECHNICAL FIELD

This invention relates to collapsible valve prostheses. Various embodiments may apply to cardiac (i.e., heart) valve prostheses including, for example, mitral valve prostheses.

BACKGROUND

Various valve pathologies, such as, in the case of cardiac valve pathologies, mitral valve pathologies (essentially stenosis or insufficiency), can be surgically treated either with "repair" techniques or with "replacement" techniques. Repair techniques, in some circumstances, may provide a higher life expectancy and less morbidity after treatment over replacement techniques. This may be related to the conservation of the native valve structures, e.g., leaflets and chordae tendineae, in the repair process, in contrast to replacement where the native valve structures are removed.

Various valve pathologies may thus benefit from the availability of arrangements permitting valve replacement (such as, e.g., Mitral Valve Replacement or MVR) in conjunction with the conservation of the native valve structures.

SUMMARY

Various embodiments may provide a collapsible valve prosthesis that can be implanted without removing the native valve leaflets and/or the native chordae tendineae.

In various embodiments, a collapsible valve prosthesis may include a sutureless anchoring portion. In various embodiments, such anchoring portion may be designed to axially anchor to the native valve site (e.g. the mitral annulus and leaflets) without appreciable radial expansion of the implant site.

In various embodiments, a valve prosthesis may include an intra-annular portion adapted to define a blood flow lumen having an inflow side and an outflow side and support therein one or more prosthetic valve leaflets, the intra-annular portion being provided with outward formations (e.g., barbs) for coupling the prosthesis to the natural valve site, e.g. the annulus, leaflets, and/or chordae tendineae.

In various embodiments, a valve prosthesis may include an over-annular portion, roughly umbrella-like, linked to the intra-annular portion and adapted to extend collar-like over the annulus of a natural valve site (e.g., in the left atrium, resting on the native leaflets and annulus of a mitral valve).

In various embodiments, the prosthetic valve leaflets may include biological tissue (optionally of the "dry tissue" type) and/or polymer.

In various embodiments, the prosthesis may be deployed at the implant site, e.g., by means of a sliding sleeve delivery system and a balloon to expand the prosthesis matching the implant site dimensions.

Various exemplary embodiments include the following:

Embodiment 1

A collapsible valve prosthesis including an armature and a set of prosthetic valve leaflets supported by the armature, the armature expandable from a contracted condition to an expanded condition for anchoring at an annulus of a natural valve site, wherein the armature includes:
a tubular intra-annular portion defining a blood flow lumen having an inflow side and an outflow side, the tubular intra-annular portion supporting the set of prosthetic valve leaflets in the blood flow lumen and being provided with outward formations for coupling with the natural valve site, and
at least one extra-annular portion linked to the intra-annular portion, the at least one extra-annular portion including an over-annular portion to extend collar-like over the annulus of the natural valve site at the inflow side of the blood flow lumen.

Embodiment 2

The prosthesis of Embodiment 1, wherein the at least one extra-annular portion linked to the intra-annular portion also includes an under-annular portion to extend collar-like at the outflow side of the blood flow lumen.

Embodiment 3

The prosthesis of Embodiment 1 or Embodiment 2, wherein the intra-annular portion and the at least one extra-annular portion are balloon-expandable and self-expandable, respectively.

Embodiment 4

The prosthesis of any of the previous Embodiments, including a sheet-like member applied onto the intra-annular portion and the over-annular portion.

Embodiment 5

The prosthesis of Embodiment 4, wherein the intra-annular portion and the at least one extra-annular portion are separate pieces linked by the sheet-like member.

Embodiment 6

The prosthesis of Embodiment 4 or Embodiment 5, wherein the outward formations of the intra-annular portion are carried by the sheet-like member.

Embodiment 7

The prosthesis of any of the previous Embodiments, wherein the intra-annular portion and the at least one extra-annular portion are separate pieces having a de-coupling member therebetween.

Embodiment 8

The prosthesis of Embodiment 4 and Embodiment 7, wherein the de-coupling member includes a length of the sheet-like member.

Embodiment 9

The prosthesis of any of the previous Embodiments, wherein the outward formations include barb-like formations.

Embodiment 10

The prosthesis of any of the previous Embodiments, wherein the outward formations include first and second formations pointing towards the inflow and the outflow sides of the prosthesis, respectively.

Embodiment 11

The prosthesis of any of the previous Embodiments, wherein the at least one extra-annular portion includes a pattern of radial finger formations.

Embodiment 12

The prosthesis of Embodiment 11, wherein the radial finger formations exhibit differential flexibility by being stiffer at their proximal ends and more flexible at their distal ends.

Embodiment 13

The prosthesis of any of the previous Embodiments, wherein at least one of the intra-annular portion and the at least one extra-annular portion includes a mesh structure.

Embodiment 14

The prosthesis of Embodiment 13, wherein the intra-annular portion includes annular members coupled via longitudinal connection members.

Embodiment 15

The prosthesis of Embodiment 13 or Embodiment 14, wherein the intra-annular portion includes a mesh structure of struts, at least one of the struts having apertures to permit application of valve leaflets onto the armature via stitching.

Embodiment 16

The prosthesis of any of the previous embodiments, the prosthesis having different axial lengths between the inflow side and the outflow side around the blood flow lumen.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

Various embodiments will now be described, purely by way of non-limiting example, with reference to the annexed figures, wherein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following description, numerous specific details are given to provide a thorough understanding of various embodiments. The embodiments can be practiced without one or more of the specific details, or with other methods, components, materials, etc. In other instances, well-known structures, materials, or operations are not shown or described in detail to avoid obscuring aspects of the embodiments. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the embodiments.

In the figures, the reference number 1 designates, as a whole, a collapsible valve prosthesis, such as a cardiac-valve prosthesis (i.e., "cardiac valve"), which can be implanted by adopting a "sutureless" approach, e.g., via non-invasive surgical techniques (e.g., thoracic (micro)surgery) or percutaneously. The general operating principles of such prostheses and the related design and implantation criteria (including details of implementation of a strictly technological nature, such as choice and treatment of the materials) are generally known in the art, which makes it unnecessary to provide a detailed description of such principles and criteria.

In various exemplary embodiments, the prosthesis 1 may include two elements, namely a support structure or armature 2, and a set of leaflets or valve sleeve 3, coupled to or applied on the armature 2 and including one or more (e.g., three) valve leaflets 3a, 3b, 3c. In exemplary embodiments, the collapsible armature 2 and the set of leaflets or valve sleeve 3 are provided as a complete set with the valve prosthesis proper (i.e. the set of leaflets or valve sleeve 3) coupled to or applied on the armature 2.

Exemplary techniques for the formation of the valve leaflets (e.g. as an assembly of sheets of biological material) and application thereof on an armature such as the armature 2 adapted for use in various embodiments are described, for example, in EP-A-0 133 420, EP-A-0 155 245, and EP-A-0 515 324, the latter document referring to the construction of a cardiac-valve prosthesis of biological tissue of the type commonly referred to as "stentless."

Figure 1:
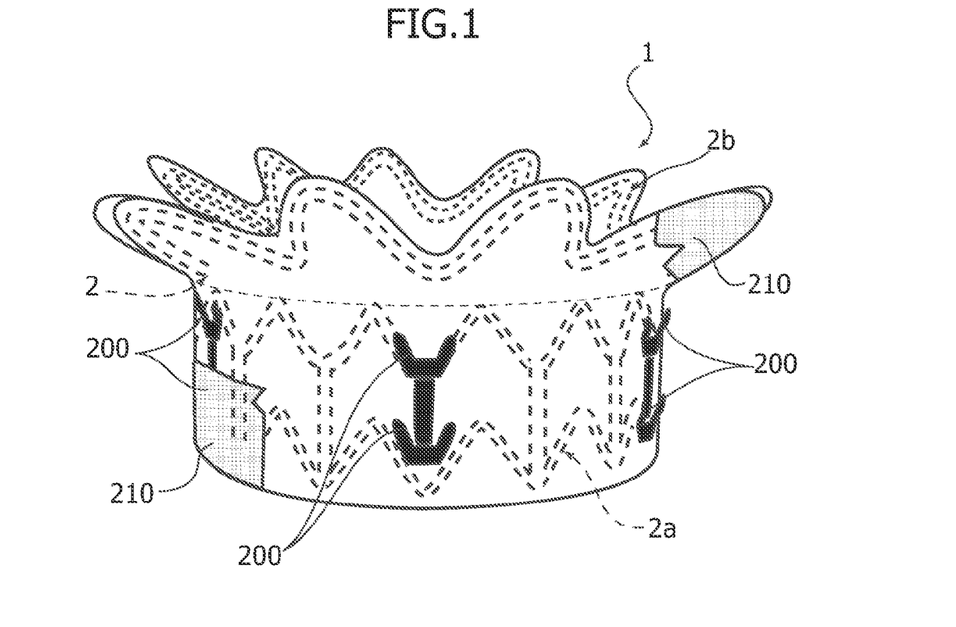
FIGS. 1 and 2 are perspective views of a valve prosthesis.

In various embodiments, the valve sleeve 3 may include a base portion 30 with an overall annular pattern, designed to extend from the portion of the valve 1, which, in the implantation site, is in an "inflow" position, i.e., a position proximal with respect to the direction of flow of the blood through the prosthesis (from top to bottom, as shown in FIG. 1). In various embodiments, starting from the base portion 30, three pleat formations 32 may extend in an axial direction towards the inside of the structure of the prosthesis 1. In various embodiments, the valve leaflets 3a, 3b and 3c may extend like a festoon, with a general claw-like conformation, between pairs of formations 32 adjacent to one another. In various embodiments, different techniques known in the art may be adopted to construct the set of leaflets 3a, 3b, 3c.

In the exemplary embodiments considered herein, the prosthesis 1 may be a valve prosthesis for use as a prosthetic mitral valve, i.e., as a valve permitting blood flow from the left atrium (inflow side) into the left ventricle (outflow side), while preventing back flow from the left ventricle into the left atrium as the left ventricle contracts to pump blood into the aorta towards the circulatory system.

In various embodiments, the leaflets 3a, 3b and 3c may exhibit a fluidodynamically proximal (i.e., "inflow") edge with an arched pattern, which extends from the base formation 30 and along two adjacent pleat formations 32; and a fluidodynamically distal (i.e., "outflow") edge, which extends towards the central orifice of the prosthesis so as to be able to cooperate (i.e., coapt) with the homologous edges of the other valve leaflets. As used herein, "fluidodynamically proximal" and "fluidodynamically distal" refer to the direction of free flow of the blood through the prosthesis, a direction that is from top to bottom as shown in the figures.

The valve leaflets 3a, 3b, 3c are able to undergo deformation, divaricating and moving up against the armature 2 (i.e., in an open position of the valve) so as to enable free flow of the blood through the valve prosthesis from an inflow to an outflow side of the blood flow lumen through valve prosthesis and the natural valve site i.e. valve annulus at which the prosthetic valve is implanted.

When the pressure gradient, and hence the direction of flow, of the blood through the prosthesis is reversed, the valve leaflets 3a, 3b, 3c move into a radially contracted position (i.e. a closed position of the valve), in which they prevent the flow of the blood through the prosthesis in the opposite direction: flow of blood through the valve prosthesis from an outflow to an inflow side of the valve prosthesis and the natural valve site (i.e. a valve annulus at which the prosthetic valve is implanted) is thus impeded.

Figure 2:
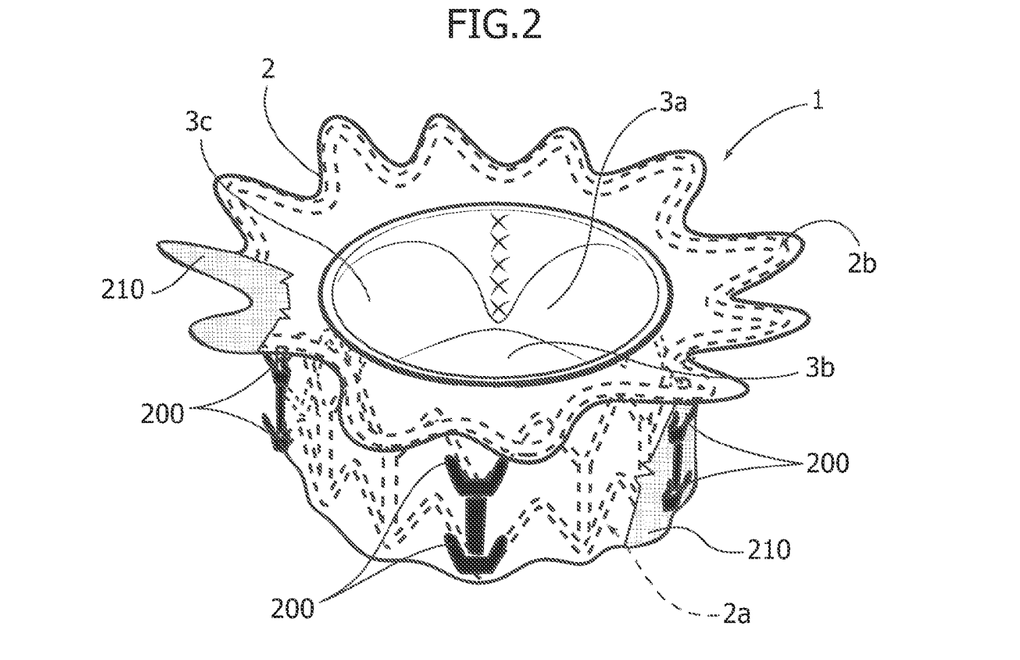

In various embodiments, the valve leaflets 3a, 3b, 3c may be made in such a way as to assume spontaneously, in the absence of external stresses, the closed position/configuration represented in FIGS. 1 and 2.

To facilitate understanding of the exemplary embodiments and certain advantages associated therewith, the rest of this disclosure will refer by way of non-limiting example to Mitral Valve Replacement (MVR) by means of a collapsible valve prosthesis 1 in conjunction with the conservation of the native valve leaflets and the native chordae tendineae.

In various exemplary embodiments, the armature 2 of the prosthesis 1 may include an intra-annular portion 2a and an over-annular (i.e. extra-annular) portion 2b linked (e.g., coupled or attached) to the intra-annular portion 2a. In various embodiments, the intra-annular portion 2a (i.e., a portion intended to extend into the native annulus through the native valve to define a blood flow lumen therein) may be configured to support the prosthetic valve leaflets 3a, 3b, 3c in the blood flow lumen. In various embodiments, the intra-annular portion 2a includes outward formations 200 for coupling with the natural valve site. In various embodiments, the formations 200 may be designed to extend at and thus "bite" into the native tissue at the interface between the annulus and any remaining native valve leaflets.

In various embodiments, the formations 200 may include barbs (e.g., sharp protrusions) adapted to penetrate (e.g., harpoon-like) into the natural tissue, e.g., into the native valve leaflets and/or into the native valve annulus. In various embodiments, the formations 200 are spread apart after the armature 2 is deployed at the natural valve site.

Figure 3:
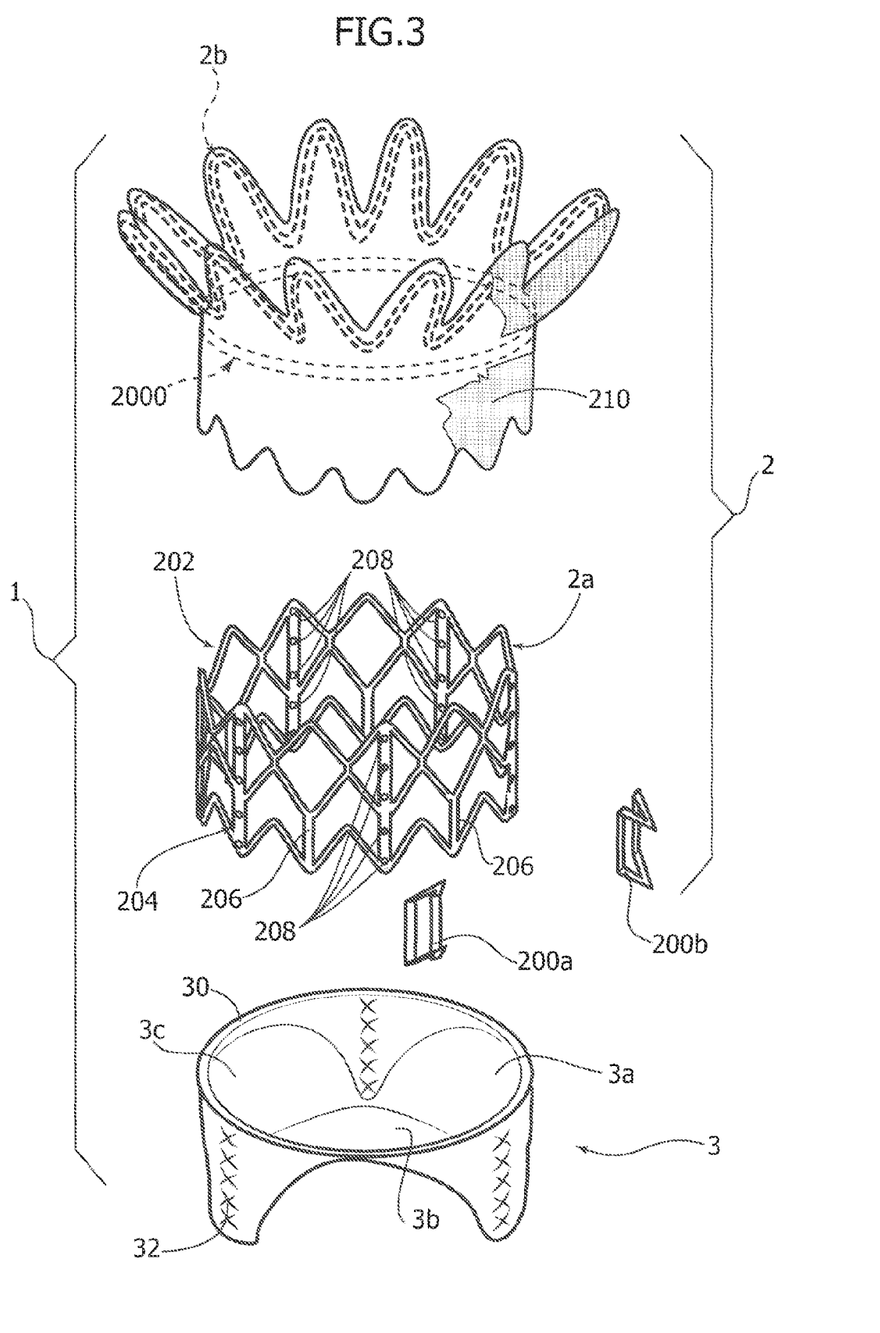
FIG. 3 is an exploded view of a valve prosthesis.

In various embodiments, the formations 200 may be angularly distributed around the prosthesis and/or may include hook-like formations. In various embodiments, these hook-like formations may include formations 200a pointing towards the inflow side and/or formations 200b pointing towards the outflow side of the blood flow lumen through the prosthesis. As shown in FIG. 3, the formations 200 include both formations 200a and formations 200b. The formations 200 or any other protrusions provided in the armature 2 may be produced one-piece (i.e., integral) with the armature 2 or may be mounted thereon as independent elements. In various embodiments, the formations 200 are coupled to the armature in such a way as to be able to "float" (i.e., be at least slightly mobile) with respect to the armature.

In various embodiments, the intra-annular portion 2a may have a radially expandable tubular pattern of, e.g., wire-like struts. Such a pattern may include a stent-like mesh structure of one or more annular members 202, 204 (circular, elliptical, or with more complex shapes, e.g., a D-shape) connected by longitudinal connections members or "links" 206. In various embodiments, the intra-annular portion 2a is formed with a cross-sectional shape that matches or approximates the cross-sectional shape of the corresponding portion of the native valve annulus. Apertures 208 may be provided in one or more of these struts (e.g., in one or more of the links 206) to permit the set of leaflets or valve sleeve 3 to be applied onto the armature 2 e.g. via stitching.

The intra-annular portion 2a may thus be functional in anchoring the armature 2 (and the valve leaflets 3 applied thereon) at the implantation site by preventing the prosthesis 1 from being displaced under the action of blood and heart pulsation while the native valve leaflets and the native chordae tendineae are retained.

The over-annular portion 2b is intended to extend collar-like over the annulus of a natural valve site (e.g., the mitral valve) at the inflow side (e.g., the left atrium) of the blood flow lumen through the prosthesis 1. In various embodiments, the over-annular portion 2b may be linked or coupled to the intra-annular portion 2a at one end thereof, e.g., at the "inflow" side of the intra-annular portion 2a, i.e., the end of the intra-annular portion 2a located upstream in the directions of free flow of blood through the prosthesis (i.e., atrial-to-ventricular in the example of mitral placement). Further, in various embodiments, the over-annular portion 2b may include a radially expandable annular (i.e., stent-like) pattern of wire-like struts.

In various embodiments, such a pattern may include a "crown-like" flared mesh structure. In various embodiments, this "crown-like" structure may include a ring-like serpentine pattern. In various embodiments, the over-annular portion 2b may include one or more radial "fingers" extending from inner, proximal ends (i.e., near the intra-annular portion 2a) to outer, distal ends. In various embodiments, an expandable ring structure is provided between the tips (i.e., the distal ends) of these finger formations. Once expanded to lie on the inflow side of the native valve site, the over-annular portion 2b may be operate to press the native biological tissue towards the outflow side (i.e., towards the upper surface of the annulus) thereby inhibiting blood leakage during normal in vivo loading.

In the exemplary embodiments, the armature 2 (and the prosthesis 1 as a whole) may be a collapsible device. The intra-annular portion 2a and the over-annular portion 2b, including the formations 200 or any other protrusions provided in the armature 2 may be made of metal (e.g. Nitinol or stainless steel), polymer or other structural material as currently admitted for use in biomedical devices such as, e.g., vascular stents. The intra-annular portion 2a and the over-annular portion 2b, including the formations 200 or any other protrusions provided in the armature 2, may be either produced one-piece or provided as independent elements linked to produce a composite structure.

In various embodiments, the armature 2 may be totally or partially covered (e.g. wrapped) with a sheath or tunic 210 of a bio-compatible material, e.g., of the type currently accepted for use in suture rings for heart valves or in vascular grafts. In various embodiments, this covering may be on the outer side of the tubular shape of the armature 2. In various embodiments, this covering may be on the inner side of the armature 2. In various embodiments, as exemplified in the drawings, this covering may be both on the outer side and on the outer side of the armature 2.

In various embodiments, the prosthesis 1 may thus include a sheet-like member applied onto the intra-annular portion 2a and the over-annular portion 2b to totally or partially cover the intra-annular portion 2a and the over-annular portion 2b of the armature 2. In various embodiments, such a sheet-like member may include biocompatible fabric (e.g. Dacron® or other polymers) and/or a biological tissue. As exemplified in the figures, the sheet-like member, e.g., the sheath or tunic 210 may be functional in providing a connection or link of the intra-annular portion 2a and the over-annular portion 2b, and optionally, the formations 200.

As shown, in certain embodiments, the formations 200 may be carried by the sheet-like member 210 (e.g., via frames stitched onto fabric or tissue) and thus be capable of "floating" or moving with respect to the prosthesis 1.

In various embodiments, the intra-annular portion 2a, the over-annular portion 2b and/or the formations 200 may be different materials. In various embodiments, the intra-annular portion 2a may include any of stainless steel (AlSI), chrome-cobalt alloys, and titanium. In various embodiments, the over-annular portion 2b may include any of Ni—Ti (e.g. Nitinol), harmonic steel, and polymers. In various embodiments, the formations 200 may include any of stainless steel (AlSI), chrome-cobalt alloys, titanium, Ni—Ti (e.g. Nitinol), and polymers.

In various embodiments, the intra-annular portion 2a may be balloon-expandable. In various embodiments, the intra-annular portion 2a may thus include a structure and/or material rendering it adapted to be expanded via a inflatable balloon or any equivalent expansion member.

In various embodiments, the over-annular portion 2b may be self-expandable. In various embodiments, the over-annular portion 2b may thus include a structure and/or material rendering it adapted to be brought to a radially contracted condition and then caused to expand e.g. by removing a constraint member confining the over-annular portion 2b to the radially contracted condition and/or change in temperature and/or various treatments.

In various embodiments, the armature 2 may thus be a composite structure including separate elements, e.g., the intra-annular portion 2a, the over-annular portion 2b, and/or the formations 200 linked via the sheet member (e.g., fabric) 210 while preserving the collapsible nature of the armature 2 or the prosthesis 1.

In various embodiments, these elements may thus be optimized independently of each other. In various embodiments, optimization may involve the selection of the materials included and/or the shape of these elements. For instance, in various embodiments the "fingers" of the over-annular portion 2b may exhibit a differential degree of flexibility. In various exemplary embodiments, the fingers are stiffer at their inner, proximal ends (i.e., near the intra-annular portion 2a) and more flexible at their outer, distal ends.

The sheet member 210 may also be functional in providing sealing at the implantation site, e.g., to counter or inhibit undesired peri-valvular blood leakage, namely blood flow around the valve and/or in avoiding undesired contact of the valve leaflets 3a, 3b, 3c to the armature 2.

In various embodiments, a de-coupling member 2000 may be interposed between the intra-annular portion 2a and the over-annular portion 2b. In various embodiments, the de-coupling member 2000 may include an annular body of a biocompatible material as the material of the sheet member 210 (e.g., a polymer). In various embodiments, the de-coupling member 2000 may include a solid or discontinuous ring-shaped formation. In various embodiments, the de-coupling member 2000 may include an axial length of the sheet member 210 separating the intra-annular portion 2a and the over-annular portion 2b.

In various embodiments, the de-coupling member 2000 may be functional in avoiding transfer of mechanical loads/stresses between the intra-annular portion 2a and the over-annular portion 2b, while optionally avoiding undesired effects (e.g. induced corrosion in a saline medium) if these portions include different materials. In various embodiments, the de-coupling member 2000 may operate to provide additional sealing at the implantation site, i.e., by countering or inhibiting undesired peri-valvular blood leakage at the interface between the intra-annular portion 2a and the over-annular portion 2b.

Figure 4:
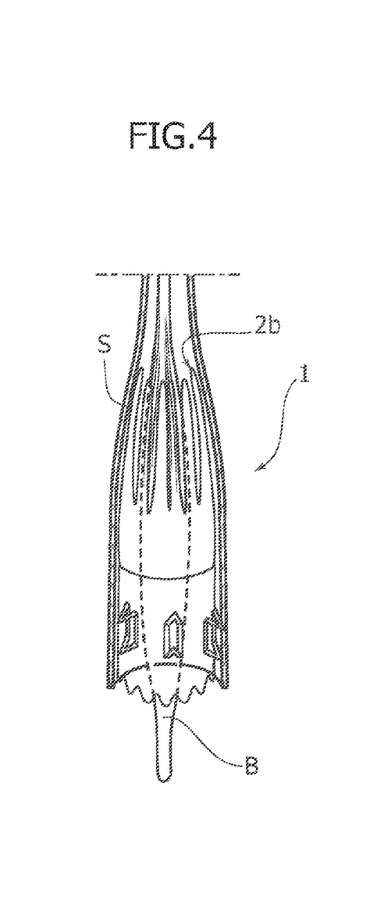
FIGS. 4 to 6 are schematically representative of implantation of a valve prosthesis.
Figure 5:
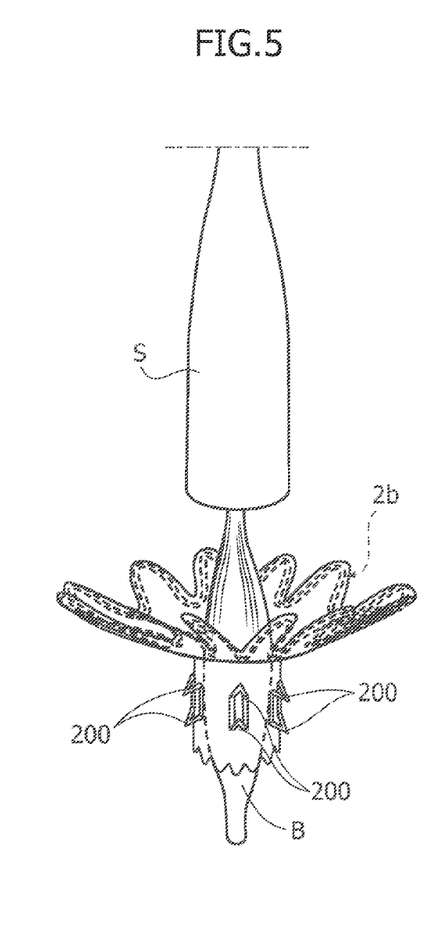
Figure 6:
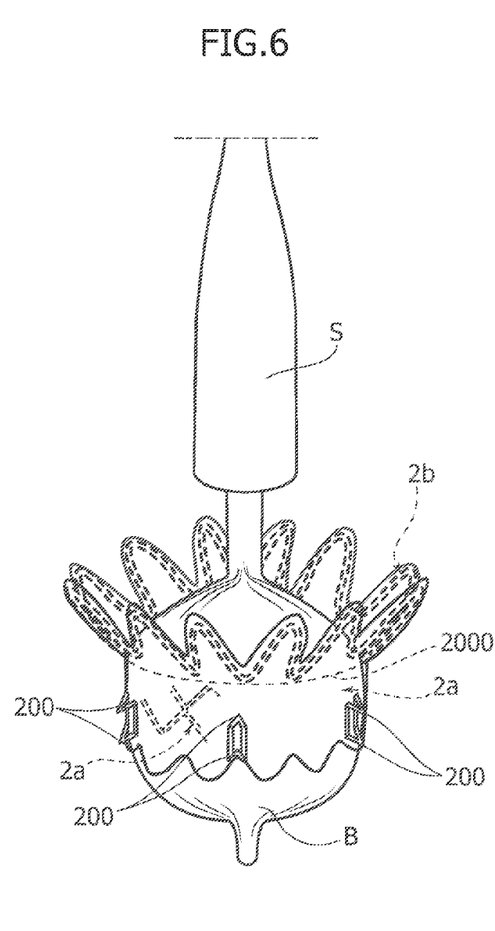

A collapsible valve prosthesis as exemplified herein can be deployed at the implant site (e.g., mitral) by resorting to sutureless (e.g., thoracic-microsurgery or percutaneous) techniques. As schematically shown in FIGS. 4 to 6, delivery and deployment may be by means of a delivery system including a sliding sleeve delivery feature S and an expandable balloon B. Such a delivery system may be configured by known criteria and means for a single access route, e.g., atrial as schematically exemplified, or for different access routes, e.g., ventricular (trans-apical).

Delivery and deployment may take advantage of the intra-annular portion 2a and the over-annular portion 2b being balloon-expandable (e.g., stainless steel, chrome-cobalt alloys, titanium) and self-expandable (e.g., shape-memory material such as Ni—Ti or Nitinol, harmonic steel, polymers), respectively.

FIG. 4 schematically represents a collapsible valve prosthesis 1 (including the armature 2 and the valve leaflets 3 applied thereon as exemplified previously) in a collapsed, radially contracted state. A containment sleeve S surrounds the prosthesis 1 (or at least the over-annular portion 2b, here assumed to be self-expandable), while the non-inflated balloon B is located within the valve leaflets 3 which are in turn surrounded and radially constrained by the intra-annular portion 2a.

Once the desired implantation location is (at least approximately) reached, the sleeve S may be retracted proximally to uncover the intra-annular portion 2a. Once the sleeve S is sufficiently retracted, the over-annular portion 2b (assumed herein to be self-expandable) will expand to an overall mushroom-like shape as schematically shown in FIG. 5. This may enable the practitioner to refine positioning of the prosthesis 1 by causing the spread-apart, over-annular portion 2b to abut against the inflow side of the native valve site, thus pressing the native biological tissue towards the outflow side (e.g., ventricular) to effectively prevent or inhibit peri-valvular blood leakage around the prosthesis.

At this point, the practitioner may actuate the expandable balloon B of the delivery system to produce the radial expansion of the valve leaflets 3 and the intra-annular portion 2a (see FIG. 6). The outward formations 200 carried by the intra-annular portion 2a may thus engage the tissue of the natural valve site to provide secure anchoring of the prosthesis at the desired implantation site without producing appreciable radial expansion. In various embodiments, balloon expandability of the intra-annular portion 2a may permit expansion to a given diameter without exerting appreciable radial stress to the implant site. In various embodiments, balloon expandability of the intra-annular portion 2a may permit to retain the prosthesis 1 crimped onto the delivery system during the whole of the delivery process, while releasing the prosthesis by deflating the balloon (only) when the desired implant condition is achieved.

In various embodiments, the over-annular portion 2b may be functional in promoting axial anchoring to the implant site, e.g., during the diastolic phase (atrium-to-ventricle blood flow in the case of a mitral valve) and countering peri-valvular leakage, e.g., during the systolic phase (left ventricle pumping blood into the aorta with the mitral valve preventing back flow into the left atrium). In various embodiments, by being expanded first (i.e., before the intra-annular portion 2a) the over-annular portion 2b may lie or rest on the native annulus and thus facilitate correct positioning of the prosthesis, whatever the implant procedure adopted, and particularly in those procedures that do not provide for direct vision of the implantation site by the practitioner.

Figure 7:
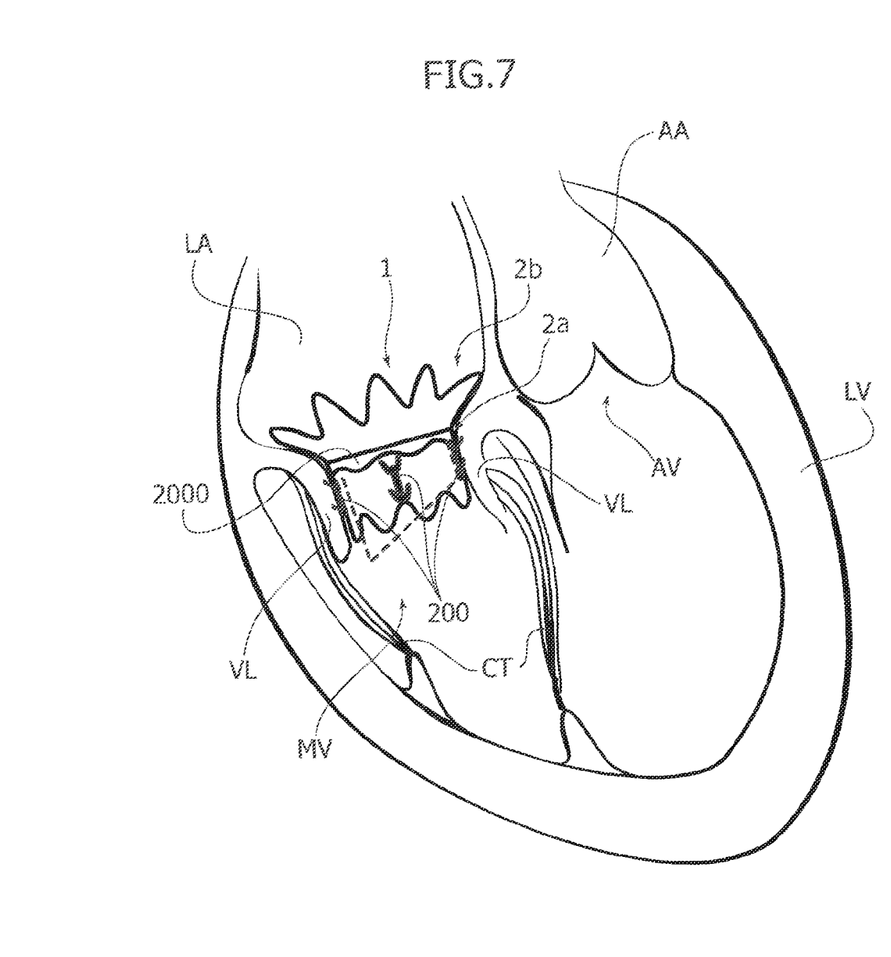
FIG. 7 is representative of a mitral application of a valve prosthesis.

FIG. 7 is a schematic representation of the left ventricle LV of a human heart with a mitral valve MV controlling the flow of blood from the left atrium LA into the left ventricle LV and an aortic valve AV controlling the flow of blood pumped from the left ventricle VL into the aorta AA. FIG. 7 is a schematic representation of the application of an embodiment for Mitral Valve Replacement (MVR) with at least substantial conservation of the structures of the native mitral valve MV, namely the mitral valve leaflets VL and chordae tendineae CT.

As shown in FIG. 7, for the exemplary case of mitral valve placement, once expanded from a contracted condition to an expanded condition for anchoring at the annulus of the natural valve site MV, the prosthesis 1 will have a final geometrical shape which will generally approximate the physiological shape and dimension of the mitral annulus.

In such an exemplary embodiment, the tubular intra-annular portion 2a will define a blood flow lumen having an inflow (i.e. atrial) side and an outflow (i.e. ventricular) side, with the tubular intra-annular portion 2a supporting the prosthetic valve leaflets 3a, 3b, 3c in the blood flow lumen, the outward formations 200 will couple with the natural valve site (essentially by penetrating into the native valve leaflets VL), and the over-annular portion 2b linked to the intra-annular portion 2a will extend collar-like over the annulus of the natural valve site at the inflow side of the blood flow lumen.

In the exemplary embodiments illustrated, the cross section of the intra-annular portion 2a (and thus the over-annular portion 2b) may be at least substantially circular; in various embodiments, the tubular intra-annular portion 2a and/or the over-annular portion 2b may have a non-circular cross section e.g. at least approximately D-shaped to more closely match the anatomy of a mitral valve.

In the exemplary embodiments illustrated, the intra-annular portion 2a is substantially cylindrical, optionally with a scalloped distal (i.e., outflow) end edge as shown in FIG. 7. In various embodiments, such a distal end edge of the annular portion 2a (and thus of the prosthesis 1) may be chamfered or beveled as schematically shown in phantom lines in FIG. 7.

In various embodiments, the prosthesis 1 may thus have a variable "height" (i.e., different axial lengths) at various angular locations of the prosthesis, that is, may have different axial lengths between the inflow side and the outflow side around the blood flow lumen, which may give rise to one or more valve tips to completely or partially mimic the anchoring portion. Such an arrangement may be functional in minimizing interaction of a prosthetic mitral valve as exemplified herein with adjacent heart districts or regions, e.g., the Left Ventricular Outflow Tract or LVOT.

Figure 8:
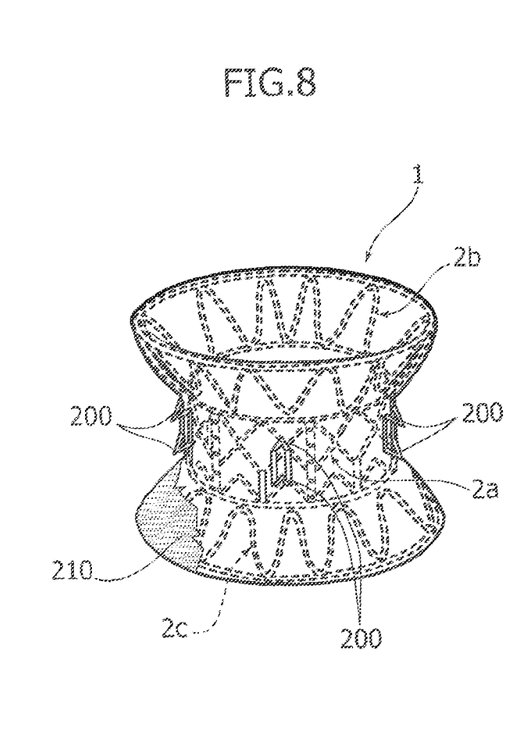
FIG. 8 is schematically representative of a valve prosthesis.

FIG. 8 is schematically representative of embodiments wherein the structure of any of the embodiments considered in the foregoing may further include an under-annular portion 2c linked to the intra-annular portion 2a to extend collar-like under the annulus of the natural valve site at the outflow blood flow lumen. In various embodiments, the under-annular portion 2c may be functional in extending towards the chordae tendineae and possibly co-operating in anchoring the prosthesis 1 at the implantation site.

In various embodiments, the armature 2 may thus include, in addition to the inter-annular portion 2a, one or two "extra-annular" portions linked to the intra-annular portion 2a, e.g., by means of the sheet member 210, namely the over-annular portion 2b and the under-annular portion 2c. Various embodiments may thus include as a (single) extra-annular portion the over-annular portion 2b which extends collar-like over the annulus of the natural valve site at the inflow side of the blood flow lumen as disclosed in the foregoing in connection with FIGS. 1 to 7.

Various embodiments may also include, in addition to the over-annular portion 2b, the under-annular portion 2c intended to extend collar-like at the outflow side of the blood flow lumen as shown in FIG. 8.

It will be appreciated that each and every feature disclosed in the foregoing with reference to the over-annular portion 2b may also apply (both as regards the structure and connection to the intra-annular portion 2a and as regards the implantation procedure) to the under-annular portion 2c, thus making it unnecessary to repeat a corresponding disclosure.

In various embodiments, this may apply i.e. to the armature 2 being a composite structure including separate elements, e.g., the intra-annular portion 2a, the two extra annular portions (namely over-annular 2b and under-annular 2c), and/or the formations 200 linked via the sheet member (e.g. fabric) 210. The over-annular portion 2b and the under-annular portion 2c (i.e. the extra-annular portions) need not necessarily be identical. Thus, in certain embodiments, the under-annular portion 2c may include one or more of the exemplary features disclosed herein in connection with the over-annular portion 2b, while such features may not be simultaneously included in the over-annular portion 2b. For instance, in various embodiments both extra-annular portions 2b, 2c may be self expandable. In various embodiments, one of the extra annular portions 2b, 2c may be self-expandable while the other may be balloon expandable. For instance, in various embodiments, the over-annular portion 2b may be self-expandable while the under-annular portion 2c may be balloon expandable.

According to one exemplary embodiment, the commissural points of the elastic collapsible valve 3 are mounted to the armature 2 such that the valve leaflets 3a, 3b, and 3c can fold and expand together. The valve 3, including the valve leaflets 3a, 3b, and 3c can be, for example, a glutaraldehyde fixed pericardium valve which has three cusps that open distally to permit unidirectional blood flow. In one embodiment, the valve member may use two pericardium sheets. The first sheet forms the three moving cusps, the second sheet coats part of the armature 2 surface so that there is no contact between the armature 2 and the valve leaflets avoiding the risk of abrasion due to repeated impact against the metallic material of the armature 2. In addition, this second sheet redistributes the stress applied by blood pressure on the prosthetic leaflets, avoiding the risk of stress concentration.

The two sheets of pericardium may be stitched together flat using suture thread coated with a film of biocompatible material, and then closed in a cylindrical shape. The type of stitch used may be varied to accommodate the directional differences in the forces exerted at each point of the suture, to ensure that the stitches themselves do not become the origin of fatigue fracture lines. The two sheets may be stitched together in a flat position so that when the leaflets open, the two sheets recover their original cylindrical configuration, forming a cylindrical duct. The elastically collapsible valve sleeve 3 can be mounted on the armature 2 by means of a number of suture stitches. Both of the sheets are useful for attaching the valve sleeve 3 to the armature 2 by stitching.

The valve member can use a tissue fixation and shaping of the leaflets 3a, 3b, 3c by means of a fluidic, atraumatic system with chemicals useful for cross-linking and then may be exposed to a detoxification post treatment to increase long-term performance. An additional pericardium sheet 30 can be positioned in correspondence with the inflow side with the purpose of improving the sealing capability of the prosthetic device with respect to the implant annulus.

In various embodiments the prosthetic valve leaflets may be different from the exemplary embodiments considered herein. In various embodiments these differences may include one or more of the following: a different number of leaflets in the set of one or more leaflets, such as e.g. two or four leaflets in the place of three; non-symmetrical sizing and positioning of leaflets; leaflets of different sizes; and/or leaflets jointly defining a non-circular shape of a blood flow lumen therethrough, e.g., an elliptical or D-shaped lumen, which more closely matches the shape of the native mitral blood flow orifice. In various embodiments the shape of the armature may be correspondingly adapted to the prosthetic valve leaflets.

Of course, without prejudice to the underlying principle of the invention, the details of construction and the embodiments may vary widely, with respect to what is described and illustrated herein by way of example, without thereby departing from the scope of protection, the extent of protection being determined by the annexed claims.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A collapsible valve prosthesis including an armature, the armature expandable from a contracted condition to an expanded condition for anchoring at an annulus of a mitral valve site bounded by a left atrium and a left ventricle, wherein the armature includes:
    a tubular intra-annular component to extend substantially entirely below the annulus of the mitral valve site when the armature is anchored at the annulus of the mitral valve site including a frame and defining a blood flow lumen having an inflow side defined by the left atrium and an outflow side defined by the left ventricle, the tubular intra-annular component being provided with outward formations for coupling with the mitral valve site,
    at least one extra-annular portion including a frame and linked to the intra-annular component, the intra-annular component and the at least one extra-annular portion being structurally separate components and including a decoupling member situated between and configured to reduce the mechanical stresses transferred between the intra-annular component and the at least one extra-annular portion, the decoupling member confined to an area within the annulus of the mitral valve site, the at least one extra-annular portion including an over-annular portion to extend, in the shape of a collar, over the annulus of the mitral valve site at the inflow side of the blood flow lumen to contact the atrial wall adjacent the annulus of the mitral valve site, and
    a set of prosthetic valve leaflets supported by the tubular intra-annular component in the blood flow lumen, the set of prosthetic valve leaflets enabling free flow of fluid through the valve prosthesis from the inflow side to the outflow side and inhibiting free flow of fluid through the valve prosthesis from the outflow side to the inflow side.

2. The prosthesis of claim 1, wherein the at least one extra-annular portion linked to the intra-annular component also includes an under-annular portion to extend, in the shape of a collar, at the outflow side of the blood flow lumen.

3. The prosthesis of claim 1, wherein the intra-annular component and the at least one extra-annular portion are balloon-expandable and self-expandable, respectively.

4. The prosthesis of claim 1, including a sheet member, formed in the shape of a sheet, applied onto the intra-annular component and the at least one extra-annular portion.

5. The prosthesis of claim 4, wherein the intra-annular component and the at least one extra-annular portion are linked by the sheet member.

6. The prosthesis of claim 4, wherein the outward formations of the intra-annular component are carried by the sheet member.

7. The prosthesis of claim 4, wherein the de-coupling member includes a length of the sheet member.

8. The prosthesis of claim 1, wherein the outward formations include barbs.

9. The prosthesis of claim 1, wherein the outward formations include first and second formations pointing towards the inflow and the outflow sides of the prosthesis, respectively.

10. The prosthesis of claim 1, wherein at least one of the intra-annular component and the at least one extra-annular portion includes a mesh structure.

11. The prosthesis of claim 1, wherein the at least one extra-annular portion includes a pattern of radial finger formations.

12. The prosthesis of claim 11, wherein the radial finger formations exhibit differential flexibility by being stiffer at their proximal ends and more flexible at their distal ends.

13. The prosthesis of claim 1, the prosthesis having different axial lengths between the inflow side and the outflow side around the blood flow lumen.

14. The prosthesis of claim 13, wherein the intra-annular component includes annular members coupled via longitudinal connection members.

15. The prosthesis of claim 13, wherein the intra-annular component includes a mesh structure of struts, at least one of the struts having apertures to permit application of valve leaflets onto the armature via stitching.

16. A collapsible valve prosthesis including an armature and a set of prosthetic valve leaflets supported by the armature, the armature expandable from a contracted condition to an expanded condition for anchoring at an annulus of a natural valve site, wherein the armature includes:
- a sheath, the sheath at least partially covering the armature,
- a tubular balloon-expandable intra-annular component to extend substantially entirely below the annulus of the natural valve site when the armature is anchored at the annulus of the natural valve site including a frame and defining a blood flow lumen having an inflow side and an outflow side, the tubular intra-annular component being provided with outward formations for coupling with the mitral valve site, and the tubular intra-annular component supporting the set of prosthetic valve leaflets in the blood flow lumen, the set of prosthetic valve leaflets enabling free flow of fluid through the valve prosthesis from the inflow side to the outflow side and inhibiting free flow of fluid through the valve prosthesis from the outflow side to the inflow side, and
- at least one self-expandable extra-annular portion including a frame and linked to the intra-annular component, the intra-annular component and the at least one extra-annular portion being separate pieces and including a decoupling member situated between and configured to reduce the mechanical stresses transferred between the intra-annular component and the at least one extra-annular portion, the decoupling member confined to an area within the annulus of the mitral valve site, the at least one extra-annular portion including an over-annular portion to extend, in the shape of a collar, over the annulus of the natural valve site at the inflow side of the blood flow lumen to contact and conform to the annulus of the natural valve site.

17. The prosthesis of claim 16, wherein the intra-annular component and the extra-annular portion have substantially the same diameter when the armature is in the contracted condition.

18. The prosthesis of claim 16, wherein the at least one extra-annular portion linked to the intra-annular component also includes an under-annular portion to extend, in the shape of a collar, at the outflow side of the blood flow lumen.

19. The prosthesis of claim 16, wherein the intra-annular component and the at least one extra-annular portion are linked by the sheath.

20. The prosthesis of claim 16, wherein the outward formations include barbs.

* * * * *